United States Patent [19]

Augustine

[11] Patent Number: 5,674,269

[45] Date of Patent: *Oct. 7, 1997

[54] PATIENT WARMING SYSTEM WITH USER-CONFIGURABLE ACCESS PANEL

[75] Inventor: Scott Douglas Augustine, Bloomington, Minn.

[73] Assignee: Augustine Medical, Inc., Eden Prairie, Minn.

[*] Notice: The portion of the term of this patent subsequent to Jul. 12, 2011, has been disclaimed.

[21] Appl. No.: 386,989

[22] Filed: Feb. 6, 1995

[51] Int. Cl.$^6$ .................................................. A61F 7/00
[52] U.S. Cl. .................................... 607/107; 607/114
[58] Field of Search ............................... 607/104, 107, 607/108–112, 114

[56] References Cited

U.S. PATENT DOCUMENTS

| | | | |
|---|---|---|---|
| 2,110,022 | 3/1938 | Kliesrath | 5/334 |
| 2,512,559 | 6/1950 | Williams | 5/347 |
| 3,757,366 | 9/1973 | Sacher | 5/347 |
| 4,139,004 | 2/1979 | Gonzalez, Jr. | 128/82.1 |
| 4,572,188 | 2/1986 | Augustine et al. | 128/380 |
| 5,106,373 | 4/1992 | Augustine et al. | 604/113 |
| 5,125,238 | 6/1992 | Ragan et al. | 62/259.3 |
| 5,165,400 | 11/1992 | Berke . | |
| 5,184,612 | 2/1993 | Augustine | 128/400 |
| 5,265,599 | 11/1993 | Stephenson et al. | 607/104 |
| 5,300,101 | 4/1994 | Augustine et al. . | |
| 5,300,102 | 4/1994 | Augustine et al. | 607/107 |
| 5,324,320 | 6/1994 | Augustine et al. | 607/107 |
| 5,336,250 | 8/1994 | Augustine | 607/107 |
| 5,343,579 | 9/1994 | Dickerhoff et al. | 5/421 |
| 5,350,417 | 9/1994 | Augustine | 607/104 |
| 5,360,439 | 11/1994 | Dickerhoff et al. | 607/104 |
| 5,383,918 | 1/1995 | Panetta | 607/104 |
| 5,443,488 | 8/1995 | Namenye et al. | 607/104 |
| 5,514,169 | 5/1996 | Dickerhoff et al. | 607/107 |

FOREIGN PATENT DOCUMENTS

| | | | |
|---|---|---|---|
| 83111871 | 11/1983 | European Pat. Off. | A61F 5/00 |
| 88309191 | 10/1988 | European Pat. Off. | A61F 7/00 |

*Primary Examiner*—Lee S. Cohen
*Assistant Examiner*—Ryan Carter
*Attorney, Agent, or Firm*—Baker, Maxham, Jester & Meador

[57] ABSTRACT

An inflatable thermal care apparatus directs a thermally-controlled inflating medium into a thermal care zone to regulate a patient's body temperature, while providing selective access to desired parts of the patient. The apparatus includes an elongate member, inflatable and formable into an enclosure that surrounds a patient and defines a thermal care zone. A plurality of exhaust ports open through sides of the inflatable member to exhaust the thermally-controlled medium. A deformally resilient, insulating access panel interconnects the sides, and extends over the patient and the enclosure to confine the inflating medium to the thermal care zone. The panel includes boundaries, such as perforations, defining sections that may be selectively removed to create temporary or permanent access openings, exposing selected regions for treatment, inspection, healing, and the like. In one embodiment, one or more predefined sections are separated along common boundaries thereof to create pliable fingers, which may be temporarily lifted to create access openings in the panel. When a finger is released, the finger's resiliency urges the finger back into place, flush with the panel. Alternatively, a pliable finger may be bent downward upon itself so that the finger's resiliency urges it against the patient's body, free from interference with the access opening. One or more sections defined by the boundaries may also be completely removed to create a permanent access opening of a selected size.

29 Claims, 4 Drawing Sheets

1

PATIENT WARMING SYSTEM WITH USER-CONFIGURABLE ACCESS PANEL

BACKGROUND OF THE INVENTION

1. Field of the Invention

The present invention relates to a system for maintaining or changing the body temperature of a hospital patient during periods of convalescence or surgery. More specifically, the invention concerns an inflatable structure filled with a thermally-controlled inflating medium that is expelled at a controlled rate to bathe the patient with the medium. A user-configurable access panel spans the patient to maintain the thermally-controlled inflating medium within a thermal care zone defined by the inflatable structure and to permit access to selected portions of the patent's body by temporarily or permanently removing predefined sections of the panel.

2. Description of the Related Art

In many cases, the body temperature of a hospital patient must be regulated by lowering or elevating it to a specific level. This is often the case with patients before, during, or after certain forms of medical treatment, such as surgery.

In the past, a pliable "blanket" has been used to control a patient's body temperature by circulating a temperature-controlled fluid through the blanket. Optimally, when the patient is covered with such a blanket, the temperature of the fluid is conducted to the patient to adjust the patient's temperature toward the desired level. However, most of the temperature exchange between the blanket and the patient occurs at the points where the blanket touches the patient's skin. In some cases, this can result in excessive heating or cooling in localized areas of the patient's skin, while little or no change occurs in the patient's overall body temperature. This approach, then, is not as efficient as some applications might require.

One alternative to the temperature-controlled blanket is the inflatable convective heating device ("the Augustine device"), described in U.S. Pat. No. 5,300,101. The '101 patent issued on Apr. 5, 1994, and is assigned to the Assignee of the present invention. The entire '101 patent is hereby incorporated herein by reference.

The Augustine device employs a flexible member that is inflated with a thermally-controlled inflating medium, and generally formable into a "U" shape which surrounds a patient. The medium is expelled through a plurality of holes in the member. This bathes the patient with the thermally-controlled inflating medium.

The Augustine device also employs one or more removable covers, affixed to the patient by adhesive strips, to help retain the inflating medium around the patient. The position of each cover may be adjusted so that both covers cooperate to selectively expose or shield a particular site on the patient's body, such as the region surrounding an incision.

The Augustine device has benefitted numerous users, many of whom have found the device to be satisfactory for their needs. The device, for example, has been recognized by many as an efficient tool for warming children. However, in certain situations, the Augustine device is not completely adequate for some users' needs. For instance, adhering the removable covers to a patient may irritate the patient's skin. Additionally, some users might benefit by having a convective heating device that provides more flexibility and convenience in exposing a specific site on the patient for surgery or examination.

SUMMARY OF THE INVENTION

The present invention concerns an inflatable thermal care apparatus to direct a thermally-controlled inflating medium into a thermal care zone to raise or lower a supine patient's body temperature, while providing selective access to desired body parts, such as surgical care sites. The apparatus includes an elongate inflatable member formable into an enclosure that surrounds a patient and defines a thermal care zone. A plurality of exhaust ports open through sides of the inflatable member, from which they expel the thermally-controlled inflating medium into the thermal care zone.

A transversely mounted access panel is generally employed to maintain the inflating medium near the patient's body, by extending across the patient and the inflatable member to confine the medium to the thermal care zone. Predefined sections of the panel defined by boundaries are independently removable to selectively provide access to portions of the patient's body. For example, the panel may include perforated boundaries that may be selectively severed to create permanent or temporary access openings to expose selected regions for treatment, inspection, healing, or other reasons. In one embodiment, adjacent sections may be separated along common boundaries to create a pliable finger, which is temporarily lifted to create a temporary access opening that reveals a selected portion of a patient's body for treatment. After treatment, the finger is released and the resilience of the panel urges the finger back into place, flush with the panel. Alternatively, the pliable finger may be bent downward upon itself to create an access opening. Here, the finger is self-positioning, since the finger's resilience urges it against the patient's body. And, the finger's position is such that it does not interfere with operations conducted through the access opening. Alternatively, one or more predefined sections may be completely removed to create a permanent access opening of a selected size.

In a specific implementation, the invention may be used to provide an inflatable thermal care apparatus for directing warmed air about a hypothermic patient, while providing selected access to body parts for inspection, treatment, healing, or the like. A different aspect of the invention includes a method of bathing selected portions of a patient in a thermally-controlled inflating fluid, using an improved thermal care apparatus. Like the apparatus of the invention, this method may be specifically implemented to treat hypothermic patients with warmed air.

The present invention affords its users with a number of distinct advantages. First, no part of the invention must be adhered to a patient. To some users, then, the invention might provide more comfort than previous arrangements. Another advantage of the invention is that the access panel provides improved flexibility in selectively exposing regions of the patient for inspection, treatment, healing, and the like. Furthermore, predefined sections of the panel may be separated along common boundaries to create one or more pliable fingers that can be positioned to expose or shield a region of the patient, as desired. If the fingers are bent downward upon themselves, their resilience urges them gently against the patient; this keeps the fingers away from the examination site and also prevents excessive loss of the thermally-controlled fluid from around the examination site and also gently orients the thermal care apparatus around the patient without adhesively attaching to the skin. Moreover, if a pliable finger and a corresponding access opening are inadvertently created in the wrong location, that finger can be abandoned, and its resilience will keep it flush with the rest of the panel, preventing fluid loss through the access opening.

The access panel may be constructed to provide a flat surface over the patient, for medical personnel to place instruments during surgery. Due to the stiffness and padding of the panel, however, the patient is completely protected from any sharp instruments that might be placed on the panel during surgery. Moreover, the manufacture of the thermal care apparatus is straightforward and economical as a result of its uncomplicated construction.

BRIEF DESCRIPTION OF THE DRAWINGS

The nature, objects, and advantages of the invention will become more apparent to those skilled in the art after considering the following detailed description in connection with the accompanying drawings, in which like reference numerals designate like parts throughout, wherein.

DETAILED DESCRIPTION OF THE PREFERRED EMBODIMENTS

General Structure

Figure 1:
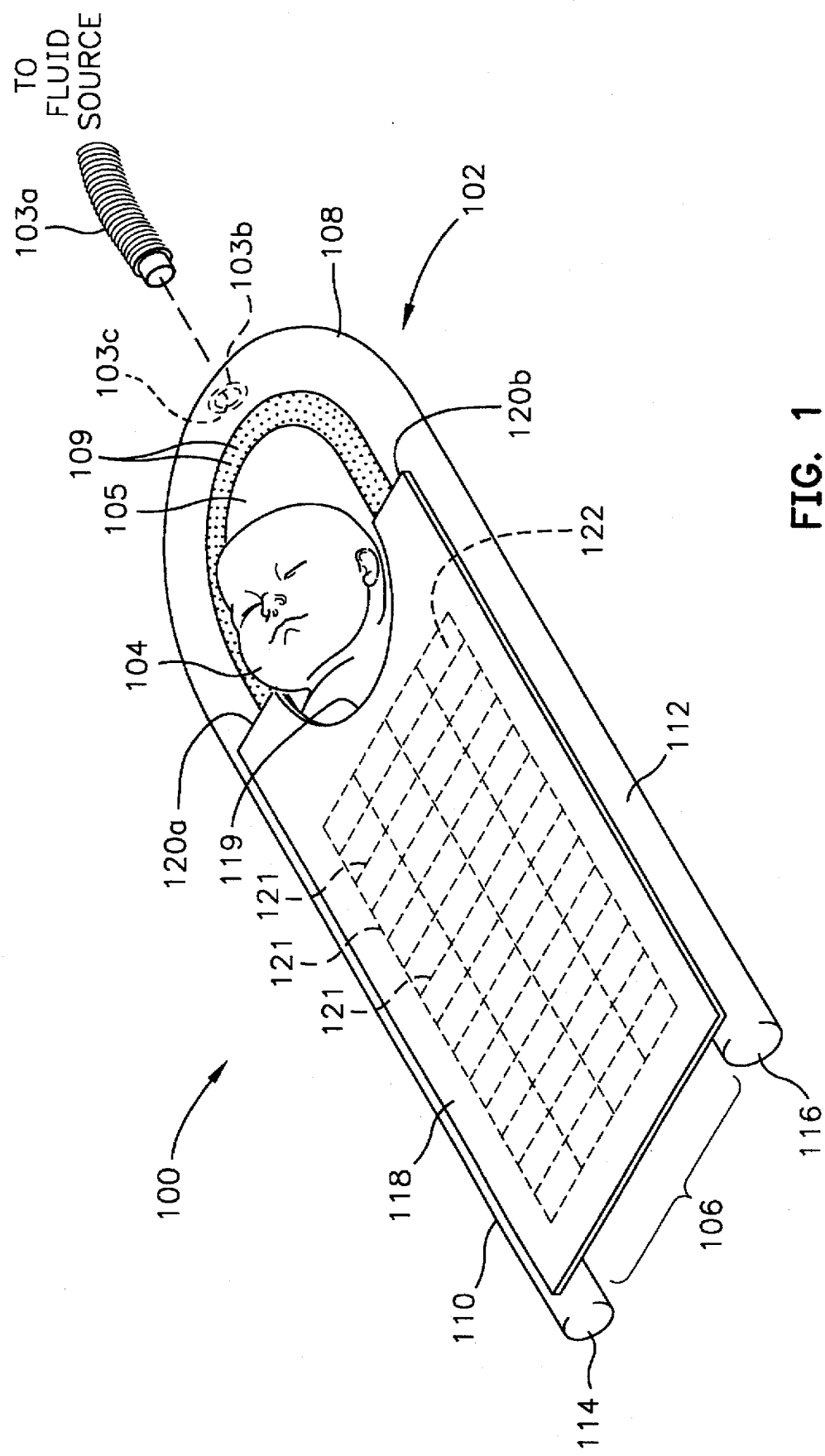
FIG. 1 is a perspective view of the thermal care apparatus 100 of the invention.
Figure 3:
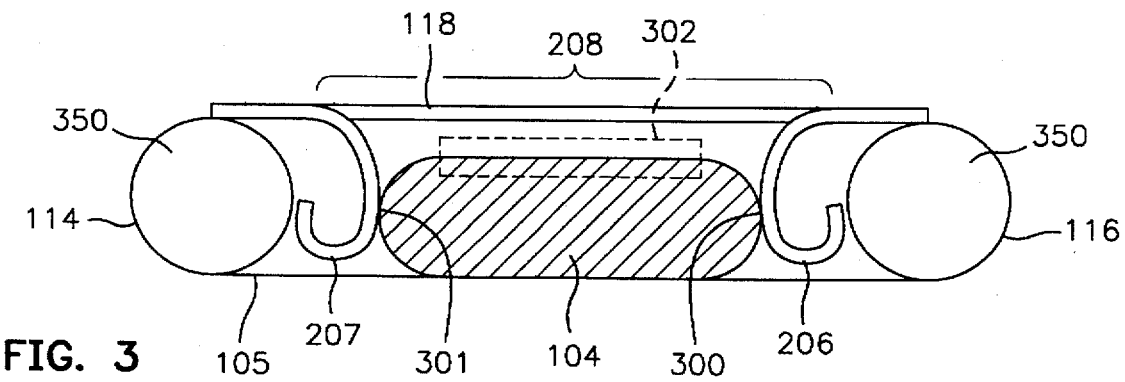
FIG. 3 is a side cross-sectional view of the thermal care apparatus 100, taken from line 3-3' of FIG. 2 and illustrating one possible configuration of the panel 118, in accordance with the invention.

Referring to FIG. 1, one aspect of the present invention comprises an inflatable thermal care apparatus 100 to direct a thermally-controlled fluid into a thermal care zone to raise or lower a patient's body temperature, while providing selective access to desired body parts, such as a surgical care sites. The apparatus 100 includes an elongated member 102, which may be inflated to define a continuous inflatable chamber 350 (FIG. 3). The member 102 has defined therein a plurality of exhaust ports 109, through which a thermally-controlled inflating medium may be expelled to bathe the patient with the medium. The medium may comprise a variety of different substances, but preferably comprises a non-toxic oxygen-based gas such as air. The member 102 receives the thermally-controlled medium from a duct 103a, which is preferably coupled to a mating base ring 103b, surrounding an inlet 103c defined in the member 102. The ring 103b is preferably formed of reinforced paper or cardboard, such as a base ring of a vacuum cleaner bag. The duct 103a is also attached to a source of inflating medium (not shown), which provides an input flow of thermally-controlled medium at a rate sufficient to fully inflate the member 102 without causing it to burst. The source, in an exemplary embodiment, comprises a heater/blower with a flow rate of 30 cubic feet per minute, such as the apparatus described in U.S. patent application Ser. No. 08/383,880, which was filed on Feb. 6, 1995 in the name of Scott D. Augustine, and is assigned to the Assignee of the present invention.

The member 102 is preferably arranged around a patient 104 who is lying supine on a surface 105 such as a hospital bed. In a preferred embodiment, the member 102 is arranged in a generally U-shaped configuration to provide a central base 108 extending to a pair of sides 110, 112, which terminate at respective terminal ends 114, 116.

The apparatus 100 also includes a user-configurable access panel 118, which interconnects the sides 110, 112. The panel 118 preferably comprises a pliant, resilient material with good insulation properties. Moreover, the panel 118 is preferably "deformably resilient", meaning that it completely or substantially returns to its original shape after being bent, folded, rolled, or similarly deformed. In the preferred embodiment, the panel 118 may comprise a ⅜ inch thickness of urethane-based foam such as 2-pound polyurethane ester, ethylene vinyl acetate blend polyethylene, or another suitable synthetic foam. Alternatively, a non-woven polyester may be used, such as a polyester having a weight of 0.7 ounces per square yard, with polypropylene extruded on one surface at 8 pounds per 3000 square feet. The panel 118 may, however, be manufactured from a variety of materials with appropriate pliancy, elasticity, thermal conductivity, rigidity, and softness for the purposes of the invention.

The panel 118, in the illustrated embodiment, comprises a generally planar rectangular member, which is secured to the sides 110, 112 and spans the patient 104. Preferably, the panel 118 is secured to the sides 110, 112 by double-sided adhesive tape, such as 3M950 EK pressure sensitive adhesive tape, manufactured by 3M of St. Paul, Minn. However, other means may be used, such as hot melt adhesives, stitching, glue, and the like.

In a general sense, the member 102, panel 118, and surface 105 cooperatively define a thermal care zone 106, within which the patient is bathed in the thermally-controlled medium. In the illustrated embodiment, the thermal care zone 106 extends from the base 108 to the terminal ends 114, 116, spanning between the sides 110, 112, and between the panel 118 and the surface 105.

The panel 118 may be located in a variety of positions. If the patient's head is to be positioned adjacent to the base 108, for example, the panel 118 is preferably spaced apart from the base 108, to avoid covering the patient's head. This type of arrangement is depicted by FIG. 1. In this embodiment, the panel 118 may be shaped to define a recess 119 and extensions 120a–120b to accommodate the patient's chin with sufficient comfort and freedom, while preventing excessive fluid from escaping the thermal care zone 106 around the patient's neck.

Although the panel 118 is shown spaced apart from the base 108, the present invention contemplates alternative positions of the panel 118, as well. The panel 118 may be mounted closer to the base 108, for instance, to cover more of the patient's head. This arrangement may be useful, for example, where the patient's head requires thermal treatment. Or, the panel 118 may be mounted with the extensions 120a–120b and recess 119 near the ends 114, 116, to accommodate a patient lying with his/her head near the ends 114, 116. A patient could be positioned with his/her head near the terminal ends 114, 116, for example, where greater thermal treatment is to be applied to the patient's lower body. Although a rectangular shape of the panel 118 is illustrated, the invention also contemplates square, trapezoidal, oval, elliptical, triangular, and a variety of other panel shapes to suit the patient's needs.

The panel 118 includes a number of predefined boundaries 121 defining removable sections (such as a section 122), to provide medical professionals convenient access to regions of interest on the patient's body. In an illustrative embodiment, the boundaries 121 may comprise perforated lines defined in the panel 118, such that desired sections of the panel 118 may be easily removed by "punching out"

selected ones of the boundaries. Alternatively, the boundaries 121 may comprise thinned narrow stripes, light adhesive seams, or complete incisions. In still another embodiment, the boundaries 121 may comprise nearly complete incisions, with thin strands of uncut material remaining at corners of the sections or other convenient locations, such that regions defined by the boundaries may be easily removed, either fully or partially. In an exemplary embodiment, the boundaries 121 define a grid of intersecting rows and columns, creating a number of removable rectangular sections, as shown by the section 122. However, the boundaries 121 may define a variety of other patterns instead, to create removable sections of other desirable shapes.

Figure 2:
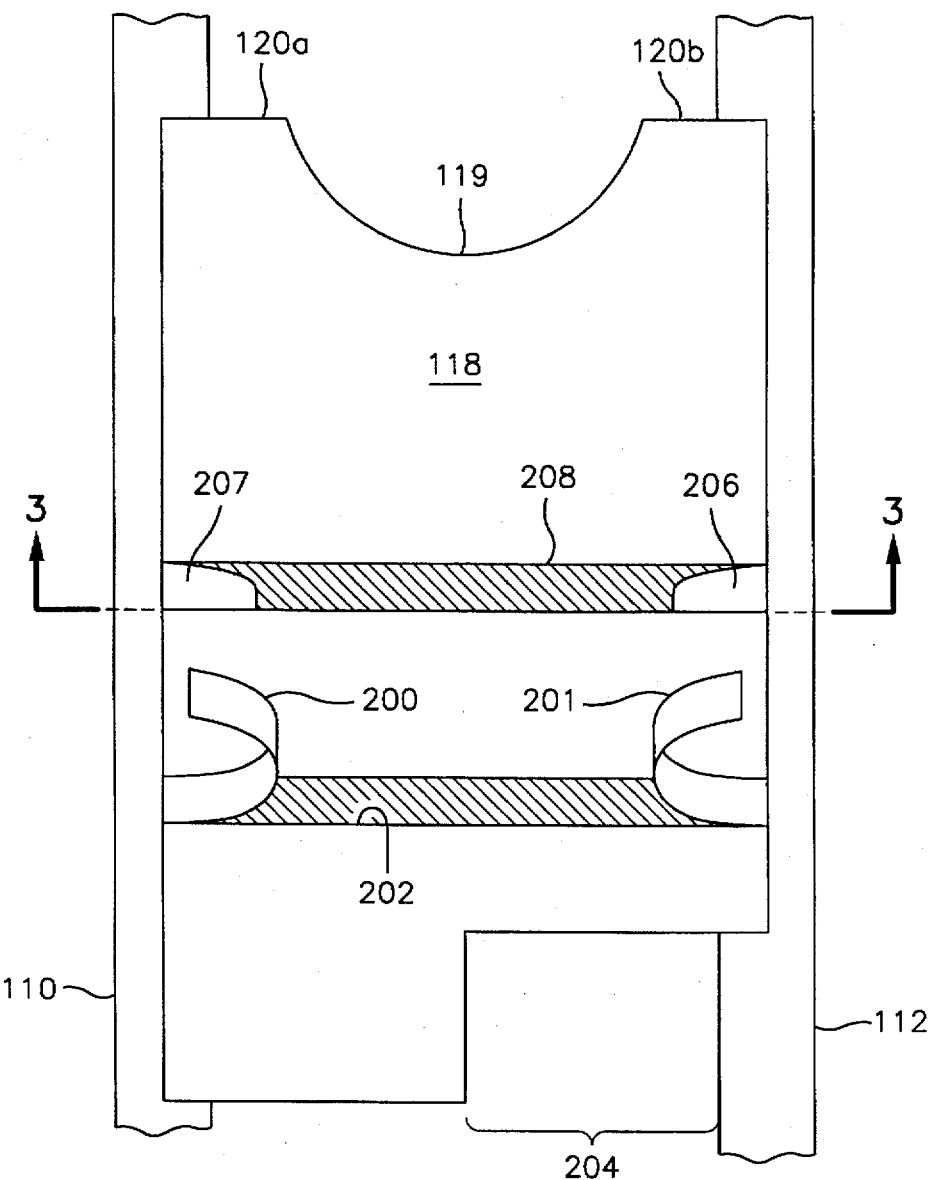
FIG. 2 is an enlarged perspective view showing a user-configurable access panel 118 of the invention in greater detail.

As shown in FIG. 2, access may be gained to a specific region of the patient by creating two pliable, opposing fingers 200–201 of material. In one embodiment, where the boundaries 121 are perforated, the fingers 200–207 are created by tearing the appropriate perforations. Creation of the fingers 200–201 is similar in embodiments where the boundaries comprise thinned stripes, lightly adhered seams, and the like. Where the boundaries 121 comprise complete incisions defined in the panel 118, the fingers 200–201 are already defined without requiring any tearing or other further severing of the boundaries 121. After the fingers 200–201 are defined (if necessary), the fingers 200–201 may be easily lifted to create an access opening 202, through which the desired region of the patient can be accessed. When finished, the fingers 200–201 may be returned to their original positions, effectively closing the access opening 202. The fingers 200–201 are urged to their original positions, flush with the panel 118, by their own elasticity. To expose a smaller area on the patient, one of the fingers 200–201 may be severed and lifted singly. Or, to oppose a larger area, two pairs of opposing fingers may be severed and lifted.

Alternatively, the appropriate perforations may be severed to completely remove one or more sections of the panel 118, thereby creating a more permanent access opening 204. As another option, perforations may be severed to create two pliable, opposing fingers 206–207 that are curled downward to create an access opening 208. The opening 208 may then be used to access a region of the patient's body. Later, the fingers 206–207 may be returned to their original positions, effectively closing the opening 208. The fingers 206–207 are urged to their original positions, flush with the panel 118, by their own resiliency.

FIG. 3 illustrates the operation of the fingers 206–207 in greater detail. With fingers 206–207 of sufficient length, the elasticity of the fingers 206–207 will urge them against contact points 300–301 on the patient's sides. This ensures that thermally-controlled inflating medium does not leak excessively through the access opening 208. With this arrangement, easy access is afforded to a desired region 302 proximate the opening 208, while the elasticity of the fingers 206–207 prevents them from interfering with the region 302.

Various other configurations of the apparatus 100 are contemplated, in addition to those described above. Although a rectangular grid of boundaries 121 is illustrated in FIG. 1, the present invention also contemplates square, triangular, circular, irregular, or other suitable patterns to meet the user's needs. Furthermore, in an embodiment where the boundaries 121 are perforated, various degrees of perforation may be used, an exemplary embodiment of the panel 118 may be constructed, for example, using 6-to-1 perforation, where each perforated line comprises an alternating sequence of 6 millimeter incisions separated by 1 millimeter lengths of uncut fabric. Also, a drape 510 (FIG. 5) may be included to assist in controlling the temperature of the patient's head.

Preferably, the diameter of the member 102, when inflated, is such that the panel 118 gently rests on the patient, ensuring that medical personnel can easily access the patient through any access openings created in the panel 118. In an illustrative embodiment, the member 102 (when inflated) is at least 2.5 inches in diameter for pediatric patients, and at least four inches in diameter for adult patients. However, other diameters may be used to accommodate patients who are sized, shaped, or positioned differently. Moreover, the member 102 may be arranged to form other shapes as needed to define other configurations of thermal care zones, the U-shaped member 102 of FIG. 1 being shown for illustrative purposes only.

Construction

Figure 4:
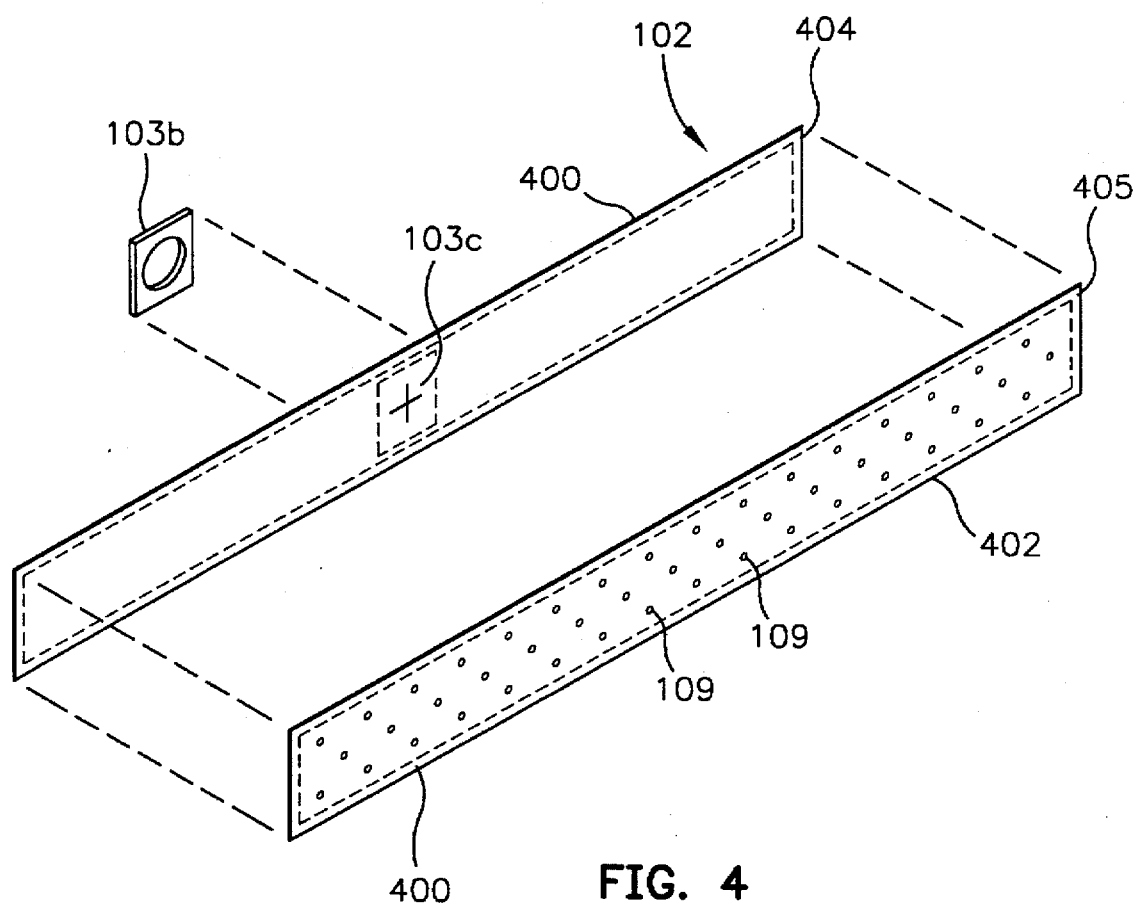
FIG. 4 is an exploded perspective view of the layers used to construct the member 102 of the invention.

Several illustrative components of the apparatus 100 are illustrated in FIG. 4, where the member 102 is shown fully elongated, not arranged in a U-shape about a patient. The member 102 is fabricated by bonding a pair of generally rectangular sheets of air-impermeable material along an air-impermeable seam. In this respect, the member 102 preferably includes a cover sheet 400 and a base sheet 402. The cover sheet 400 is formed, in the preferred construction, from a single layer of flexible plastic sheet material. The cover sheet 400 preferably comprises a plastic material such as a sheet of 0.001 inch thickness K5085 polypropylene resin manufactured by Himont Corp. of Mankato, Minn. The base sheet 402 preferably comprises a first layer made from a fibrous material such as heat sealable plastic extruded over or bonded to a second layer made from absorbent tissue paper or another synthetic material.

To form the member 102, a plurality of exhaust ports 109 are first opened through the base sheet 402 prior to bonding the cover and base sheets. The exhaust ports 109 are preferably made with $\frac{1}{16}$ inch diameter holes, which may be arranged in a pattern such as a rectangular grid. Next, the inlet aperture 103c is defined in the cover sheet 400, and the base ring 103b is attached to the cover sheet 400 about the inlet aperture 103c. Then, the cover sheet 400 is heat bonded to the base sheet 402 along their common peripheries 404–405. The sheets 400, 402 are bonded along the peripheries 404–405 to create a peripheral seam 500 (FIG. 5) around the perimeter of the sheets 400, 402.

Having described the structure of the member 102, it can be seen that flowing an inflating medium into the inlet aperture 103c fills the interior of the sheets 400, 402 with the medium. This results in the inflation of a tubular-shaped chamber 350 (FIG. 3), which exhausts medium from its interior through the exhaust ports 109 to provide an effective seal against the inflating medium. The peripheral seam 500 preferably has a width of $\frac{1}{2}$, or another suitable dimension. Depending upon the rate at which the inflating medium is injected into the member 102, it may be desirable to utilize a seal 500 that defines intermittent vents 501 (FIG. 5) designed to release inflating medium therethrough at a controlled rate. The vents 501 may, in an illustrative embodiment, be about 0.75 inch wide.

Although FIGS. 1 and 4 illustrate the placement of the inlet aperture 103c at the base 108, other arrangements may also be possible. However, the inlet aperture 103 is preferably placed so as to maintain a uniform temperature profile along the inflatable member 102. As an example, a pair of inlets (not shown) may be provided at the ends 114, 116.

Figure 5:
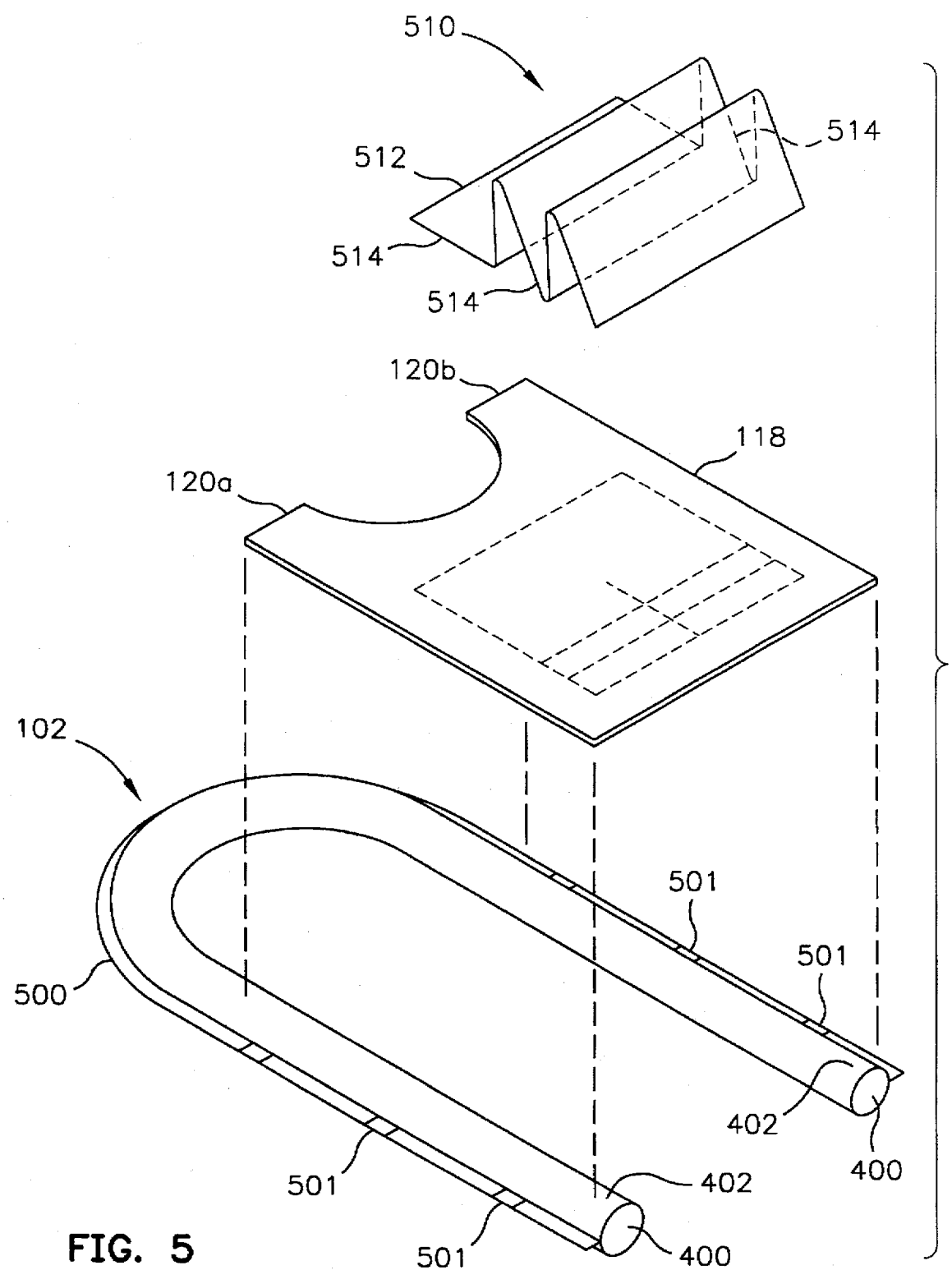
FIG. 5 is a perspective view illustrating the assembly of the member 102 and the panel 118 of the invention.

After the member 102 is constructed, the access panel 118 is aligned with the member 102 as shown in FIG. 5, and then the two components are adhered to each other. In an exemplary embodiment, the panel 118 is adhered to the sides 110, 112. However, other adherence points may be employed where the base sheet 402 is oriented inward toward the thermal care zone 106, such that the exhaust ports 109 cooperate to bathe a common area.

As shown in FIG. 5, a drape 510 may also be included to assist in regulating the temperature of the patient's head. The drape 510 comprises a width of insulating material that, in a preferred embodiment, is temporarily ribbon-folded and detachably bound to the panel 118. To avoid excessive loss of the thermally-controlled fluid around the patient's head, the drape 510 may be unfolded and placed over the patient's head.

The drape 510 preferably comprises a clear insulant such as polyethylene or another suitable material. The drape 510 is securely fastened to the panel 118 along an edge 512. Additionally, overlapping points of the ribbon-folded drape 510 are temporarily bonded at contact points 514. Bonding of the contact points 514 may be accomplished with heat, or another means that provides a sufficiently sturdy but conveniently broken joint between overlapping layers of the drape 510.

Method of Operation

Referring now to all Figures, the thermal care apparatus 100 provides a thermal care zone 106 within which a patient 104 may be placed. First, the patient 104 is placed supine on a flat surface 105, such as a hospital bed. Then, the apparatus 100 is placed over the patient 104, with the sides 110, 112 generally parallel to the patient's sides. The access panel 118 is centered over the patient's torso. Then, the inlet duct 103a is coupled to the base ring 103b, and the source of inflating medium is activated to fill the member 102 with thermally-controlled inflating medium.

Depending upon the size of the member 102, it may be used to treat anyone from a small child to an adult. The patient 104 may be positioned as shown in FIG. 1, or in another orientation such as a reversed position with the patient's head placed at the ends 114, 116. The patient 104 may receive thermal care from the apparatus 100 before, during, or after medical treatment. During use of the apparatus 100, the ends 114, 116 of the inflatable member 102 are maintained next to the patient 104 by the interconnection between the member 102 and the panel 118. In this configuration, the exhaust ports 109 direct the thermally-controlled inflating medium outward from the inflatable chamber 350, and toward the patient 104, who rests within the thermal care zone 106. The panel 118 helps retain the thermally-controlled inflating medium around the patient.

While there have been shown what are presently considered to be preferred embodiments of the invention, it will be apparent to those skilled in the art that various changes and modifications can be made herein without departing from the scope of the invention as defined by the appended claims.

What is claimed is:

1. A thermal care apparatus for bathing a patient in a thermally-controlled medium, said apparatus comprising:

an elongated inflatable member, wherein said member when inflated generally forms a U-shape having a base and a pair of opposing sides defining a thermal care zone, said member having a plurality of exhaust ports defined therein for exhausting a thermally-controlled inflating medium into the thermal care zone;

an inlet secured to the member to receive the thermally-controlled inflating medium into the member; and a substantially flat panel interposed between the opposing sides and secured thereto.

2. The apparatus of claim 1, wherein the panel defines boundaries for creating at least one selectively removable section in the panel.

3. The apparatus of claim 2, wherein the boundaries comprise perforated regions in the panel.

4. The apparatus of claim 3, wherein the boundaries form a rectangular grid.

5. The apparatus of claim 3, wherein the boundaries are shaped such that access openings of selected sizes may be created by severing selected regions of the boundaries.

6. The apparatus of claim 1, wherein the panel has sufficient resiliency to substantially retain its shape after being deformed.

7. The apparatus of claim 3, wherein the boundaries are shaped such that severing selected regions of the boundaries creates a pliable finger that temporarily creates an opening in the panel while the finger is lifted from or pushed into the panel.

8. The apparatus of claim 1, wherein the panel comprises a thermal insulant.

9. The apparatus of claim 1, wherein the panel comprises a layer of synthetic foam.

10. The apparatus of claim 1, wherein the thermally-controlled inflating medium comprises air.

11. The apparatus of claim 1, wherein the thermally-controlled inflating medium comprises heated air.

12. The apparatus of claim 1, wherein the thermally-controlled inflating medium comprises cooled air.

13. The apparatus of claim 1, wherein the member comprises at least two sheets of air impermeable material joined at the peripheries of said sheets with an air impermeable seam.

14. The apparatus of claim 1, wherein the exhaust ports are arranged in a grid of rows and columns.

15. The apparatus of claim 1, further comprising a source of thermally-controlled inflating medium sealingly connected to the inlet to inflate the member by injecting the thermally-controlled inflating medium into the chamber.

16. The apparatus of claim 1, wherein the member further defines at least one vent therein to release fluid at a selected rate when the chamber is inflated.

17. The apparatus of claim 1, further comprising a drape secured to the member to retain the inflating medium in the thermal care zone when placed thereover.

18. A thermal control apparatus for selectively bathing body portions of patient in a thermally-controlled inflating medium comprising:

an inflatable member for positioning about a thermal care zone to form a thermal bathing structure with at least one closed end and including sides for disposition laterally to said thermal care zone, said sides having defined therein a plurality of exhaust ports for exhausting a thermally-controlled inflating medium from said body to said thermal care zone;

an inlet in fluid communication with the member for receiving the thermally-controlled inflating medium into the member; and a panel secured across the sides of the member.

19. The apparatus of claim 18, wherein the panel includes selectively removable sections to selectively expose body portions in the thermal care zone.

20. The thermal control apparatus of claim 18, wherein the thermal bathing structure includes a transverse base and a pair of generally longitudinal sides to form a U-shape.

21. The thermal control apparatus of claim 18, wherein the member forms a single tubular structure when inflated, said single tubular structure including:

a base sheet having a plurality of apertures defined therein; and a cover sheet bonded to said base sheet by a peripheral seam.

22. A method for bathing selected portions of a patient in a thermally-controlled inflating medium, comprising the steps of:

supporting a patient to be treated on a support surface;

arranging an inflatable thermal care apparatus around the patient to form a structure with two sides and a closed end defining a thermal care zone containing the patient, said apparatus including an inflatable member in communication with an inlet for receiving a thermally-controlled inflating medium into said member to inflate the member, said member having a plurality of exhaust ports defined therein for exhausting the inflating fluid from the body to the thermal care zone, said apparatus further including a panel secured to the sides and spanning the thermal care zone;

connecting the inlet to a source of a thermally-controlled inflating medium capable of inflating said member; and exhausting the thermally-controlled inflating medium through the exhaust ports.

23. The method of claim 22, further comprising the steps of:

defining at least one access opening in the panel by separating at least one selected predefined section defined in the panel; and accessing selected body portions of the thermal care zone through at least one of the access openings.

24. The method of claim 23, wherein the defining step comprises the steps of severing perforated boundaries defined in the panel to completely separate one or more sections of the panel, and removing the separated sections.

25. The method of claim 23, wherein the defining step comprises the steps of severing perforated boundaries defined in the panel to create one or more fingers.

26. The method of claim 25, wherein the accessing step comprises the steps of lifting at least one finger to expose selected body portions of the patient.

27. The method of claim 25, wherein the accessing step comprises the steps of depressing at least one finger to expose the selected body portions while said at least one finger is self-retained against the patient's side.

28. The method of claim 22, further comprising a step of exhausting fluid at a selected rate through vents defined in the inflatable member.

29. The method of claim 22, further comprising a step of covering the patient's head with a head drape attached to the inflatable thermal care apparatus to retain the inflating medium proximate the patient's head.

* * * * *